United States Patent [19]

O'Lenick, Jr. et al.

[11] Patent Number: 4,867,750
[45] Date of Patent: Sep. 19, 1989

[54] ALKOXYLATED POLYESTERS

[75] Inventors: Anthony J. O'Lenick, Jr., Lilburn; Randy L. Rayborn, Winder, both of Ga.

[73] Assignee: GAF Corporation, Wayne, N.J.

[21] Appl. No.: 282,729

[22] Filed: Dec. 12, 1988

Related U.S. Application Data

[60] Division of Ser. No. 178,423, Apr. 20, 1988, Pat. No. 4,824,606, which is a continuation-in-part of Ser. No. 50,089, May 14, 1987, abandoned.

[51] Int. Cl.$^4$ .................. C09K 2/10; C07C 69/74; C07C 69/76
[52] U.S. Cl. .................... 8/115.51; 8/127.5; 8/127.51; 252/607; 252/609; 560/91; 560/120; 528/299
[58] Field of Search .............. 427/393.3, 393.4; 528/299; 560/91, 120; 252/607, 609; 8/116.4, 127.5, 127.51, 115.51

[56] References Cited

U.S. PATENT DOCUMENTS

| | | | |
|---|---|---|---|
| 4,098,704 | 7/1978 | Sandler | 252/8.6 |
| 4,696,954 | 9/1987 | Pritchard | 521/167 |
| 4,713,194 | 12/1987 | Gosselink | 252/174.23 |
| 4,824,606 | 4/1989 | O'Lenick | 252/607 |

FOREIGN PATENT DOCUMENTS 1263949  11/1986  Japan .................. 560/120

Primary Examiner—John F. Niebling
Assistant Examiner—Isabelle Rodriguez
Attorney, Agent, or Firm—Marilyn J. Maue; Joshua J. Ward

[57] ABSTRACT

The invention relates to a polymer having the structure

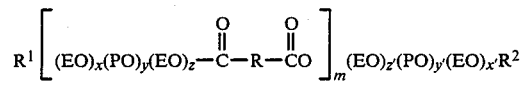

and mixtures thereof wherein R is a perhalogenated aromatic or cyclo aliphatic radical containing from 6 to 7 carbon atoms in the cyclic structure; $R^1$ is hydroxy or $C_1$ to $C_{10}$ alkoxy; $R^2$ is hydrogen or $C_1$ to $C_{10}$ alkyl; EO represents the radical —$CH_2CH_2O$—; PO represents the radical

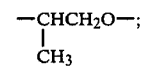

m is an integer having a value of from 6 to 20; and x, y, z, x', y' and z' each represent an integer having a value of from 0 to 50 with the proviso that the sums of x+y+z and of x'+y'+z' are greater than 5.

The application is also directed to the preparation and use of the above polymer.

15 Claims, No Drawings

ALKOXYLATED POLYESTERS

This is a division of application Ser. No. 178,423, filed Apr. 20, 1988, now U.S. Pat. No. 4,824,606, copending U.S. patent application Ser. No. 050,089, filed May 14, 1987, entitled "FIRE RESISTANT SOIL RELEASE COMPOUNDS", which was filed in the names of Anthony J. O'Lenick, Jr. and Randy L. Rayborn, now abandoned.

In one respect the invention relates to novel alkoxylated polyesters.

In another aspect the invention relates to the preparation of said polyesters and to their use as fire resistant and soil release agents.

BACKGROUND OF THE INVENTION

Extensive research has been devoted to the discovery of coumpounds having good flame retardancy, substrate substantivity and soil release properties. The combination of these properties in one compound would avoid the need for multicomponent formulations. Many chemicals have been developed with this aim in mind but have been found lacking in at least one of these properties. For example, the compounds of U.S. Pat. No. 4,098,704 have been developed primarily for flame retardant coatings for fabrics which incidentally forms a barrier for deposition of soil. These compounds are composed of polyalkoxylated compounds containing a single aromatic group and have been found to lack substantivity toward nonionic substrates. Further, these chemicals tend to precipitate from formulations containing cationics.

U.S. Pat. No. 4,125,733 also describes flame retardant compounds which contain alkyl bromonated moieties and free carboxyl groups in their structure thus making them highly anionic. The brominated terminal group of the compound causes yellowing of fabric and lowering of color brightness. Further, the strongly anionic character attributed to the reactive free carboxyl groups causes precipitation in cationic envrionments and molecular instability.

Still other compounds developed for flame retardancy include those disclosed in U.S. Pat. No. 3,278,580 which are hydrophobic, high molecular weight materials having little or no substantivity to fabrics. Further, coating with the chemicals of this patent significantly reduces the flexibility of the fabric. The monocyclic compounds disclosed in this patent lack soil removal properties and are more or less restricted to rigid or flexible polyurethane foams.

It is another object of this invention to provide a compound having good soil release and flame retardant properties together with high substantivity to Keratinous substrates and cellulose, polyester and cotton materials such as fabrics and paper, while additionally providing good water wicking characteristics.

Another object of the invention is to provide an economical and commercially feasible method of producing a flame retardant, soil release substantive product suitable for many applications in washing, rinsing and in coating substrates of various types.

These and other objects will become apparent from the following description and disclosure.

THE INVENTION

In accordance with this invention there is provided a lipophilic-hydrophilic polyester having the structure:

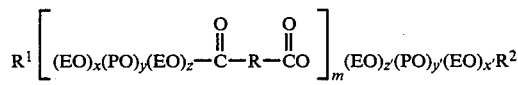

wherein AO is $C_2$ to $C_3$ alkylene oxide which, when present as a mixture of ethylene oxide and propylene oxide units, can occur in random or block distribution; v and v' are each integers having a value of from 5 to 150; m is an integer having a value of from 3 to 22; R is an aromatic or cyclo aliphatic radical containing from 6 to 7 ring carbon atoms and at least 3 chlorine or bromine atoms bonded to the cyclic ring, any remaining ring substituents being either hydrogen or lower alkyl; $R^1$ is hydroxy or $C_1$ to $C_{10}$ alkoxy and $R^2$ is hydrogen or $C_1$ to $C_{10}$ alkyl.

A species of the above compound is represented by the formula:

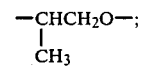

and mixtures thereof wherein R, $R^1$ and $R^2$ are as described above; EO is ethylene oxide having the structure $-CH_2CH_2O-$; PO is propylene oxide having the structure $$-CHCH_2O-;$$
$$\phantom{-}|\phantom{CH_2O-;}$$
$$\phantom{-}CH_3$$

m is an integer having a value of from 3 to 22; x, y, z, x', y' and z' each represent an integer having a value of of from 0 to 50 with the proviso that each of the sums of $x+y+z$ and $x'+y'+z'$ are greater than 5. Of this group, those compounds wherein R is a perhalogenated radical and y, z, y' and z' are positive integers are preferred. The R group of the present compounds can be represented by the divalent radicals having the structure

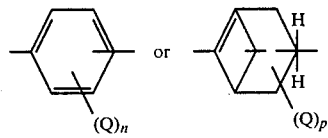

wherein Q is chlorine or bromine; n has a value of 3 to 4 and p has a value of 2 to 6, of which R groups wherein n is 4 and p is 6 and m is greater than 5 are preferred.

Included in the preferred polyester compounds of this invention are polytetrahalonorbornene dicarboxylic diol and polyperhaloterephthalic diol both esterified with between 12 and 20 EO units and between 2 and 4 PO units and containing 10 to 20 polyperhaloterephthalic units or polytetrahalobornene dicarboxylic units.

The polymers of this invention possess superior soil release, wicking and fire retardant properties together with outstanding substantivity for polyester, cellulosic and Keratinous substrates. The higher molecular weight compounds of this group are excellent viscosity builders which find many uses, particularly in hair shampoo since they are non-toxic and are easily removed by rinsing with water so as to prevent chemical build-up on the hair. These compounds find many applications in cosmetic formulations and laundry detergents as well as textile finishing to provide fire retardancy to polyester and cotton fabrics. They are also useful as paper coating to provide better receptivity to printing ink.

In accordance with this invention, polymers wherein m is greater than 5, preferably greater than 15, can also contain an amount of non-halogenated cyclic R groups, preferably a minor amount of such non-halogenated species, i.e.

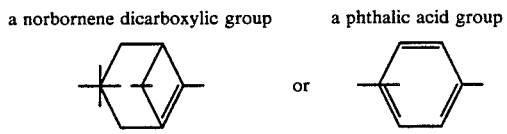

a norbornene dicarboxylic group    or    a phthalic acid group in order to increase substantivity to polyester fiber and skin for use in sun tan lotions. Although, the EO and PO units of the present polymer are preferably arranged in block structure, it is within the scope of this invention random distribution is also permissible. It is to be understood however, that the arrangement of EO and PO blocks may be rearranged where desired so that the capping groups of the cyclic moiety could be —(-PO)$_{y'}$(EO)$_x$(PO)$_{y''}$—wherein y'' has a value in the range of y.

The present alkoxylated polyesters are prepared by an economical and commercially feasible process which involves esterification by reacting a polyhalogenated cyclic dicarboxylic compound corresponding to group R in the above formula with a polyalkoxylated alcohol containing from 2 to 6 terminal hydroxy groups, e.g. a diol or glycol such as polyalkoxylated ethylene glycol, polyalkoxylated propylene glycol, ethylene glycol, block polymers of polyethylene and polypropylene glycols, glycerol, diethylene glycol, sorbitol, etc.

Examples of dicarboxylic acid reactants containing the R structure include 1,4,5,6,7,7-hexachlorobicyclo (2-2-1)-5-heptene-2,3-dicarboxylic acid; 1,4,5,6,7,7-hexachloro-2-methylbicyclo-(2,2,1)-5-heptene-2,3-dicarboxylic acid; tetrachlorophthalic acid; trichlorophthalic acid; 2-methyl-trichlorophthalic acid and corresponding brominated or brominated analogs of the these compounds. As indicated above, the reaction mixture may optionally include a minor amount of a non-halogenated phthalic acid or cyclohexenedicarboxylic acid. The non-halogenated component can be employed in an amount up to about 20 wt. % of the halogenated reactant.

In general, the reaction is effected with a molar excess of the polyhydroxy compound, preferably within the range from about 2:1 to about 5:1, with respect to the cyclic reactant. An inert diluent can be used in the reaction to provide a reaction mixture containing from about 100% to about 10% by weight of reactive components. Suitable diluents include non-protic high boiling solvents, e.g. diglyme.

The esterification may be assisted by an esterification catalyst such as, for example, tin oxide; p-toluene sulfonic acid; magnesium oxide; organotitanates, e.g. dilauryl titanate; organo tin compounds e.g. dibutyl tin laurate, dilauryl tin oxide, etc. of which p-toluene sulfonic acid is preferred. The conditions employed include a temperature of between about 140° C. and about 220° C. under a pressure of from about atmospheric to about 20 mm Hg for a period of from about 1 to about 16 hours. Preferred conditions include a temperature ranging between about 180° C. and about 200° C., under atmospheric pressure for a period of 5 to about 8 hours. The preferred procedure involves introducing the cyclic component to the prepolymerized polyhydroxy reactant, agitating the mixture during esterification to maintain good contact while distilling off water of reaction. Upon completion of the reaction at the cession of generated water by product, the reaction mixture is cooled and the product is recovered as a solid. The solid product can be ground or flaked for use as a granular solid or it can be formed into a homogeneous dispersion with a suitable inert carrier, e.g. water for applications involving textiles or cosmetic formulations; mineral oil or linseed oil for use in roofing materials; toluene for use in paints and varnishes, to name a few.

The products of the present process can be used directly in an aqueous solution as coatings for textiles or cellulosic materials, or added to existing formulations such as cosmetic, laundry detergent or textile coating formulations to impart their fire retardant, soil releasing properties. In either case, the concentration of the present compounds in such compositions can vary between about 0.001 and about 12% by weight, preferably between about 0.1% and about 5% by weight. Addition of the present lipophilic-hydrophilic products simplifies formulation and reduces the number of components which need be added to achieve flame retardancy, soil release, wicking, substrate substantivity and other beneficial properties.

Having thus generally described the invention, reference is now had to the following examples which illustrate preferred embodiments and comparisons with commercial products but which are not to be construed as limiting to the scope of the invention as more broadly described above and as set forth in the appended claims.

All amounts and proportions recited in the examples are by weight unless otherwise indicated.

EXAMPLE 1

Into a sealed glass 3 necked flask, equpped with a mechanical stirrer and a reflux condenser, was introduced 155.70 grams of 1,3-isobenzo-4,5,6,7-tetrachloro furandione

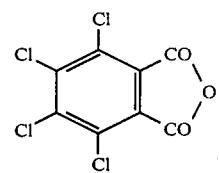

844.30 grams of polyoxyethylene having a molecular weight of 1540 and 1.0 gram of p-toluene sulfonic acid. The mixture was purged with nitrogen to provide an oxygen free atmosphere and was then stirred and heated slowly to 160°–180° C. while continuously distilling off water of reaction and allowing the viscosity of the product to increase until 98% of the water is removed. The liquid product containing

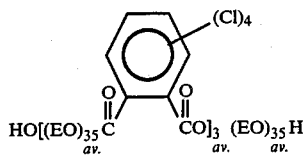

is then cooled and recovered. The product analyzed at 7.85 wt. % organic chlorine.

EXAMPLE 2

Example 1 was repeated, except that 844.30 grams of a random 1:1 molar ethyleneoxide/propylene oxide polymer having a molecular weight of 1540 was substituted for the ethyleneoxide polymer and 1 g. of dibutyl tin laurate catalyst was substituted for p-toluene sulfonic acid. The product containing

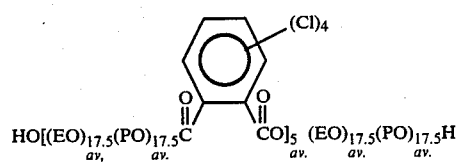

was analyzed at 7.85 wt. % organic chlorine.

EXAMPLE 3

Into a sealed glass 3 necked flask, equipped with a mechanical stirrer and a reflux condenser was introduced 87.70 grams of 1,3-isobenzofuranedione-4,5,6,7-tetrachloro and 921.30 grams of ethylene oxide polymer having a molecular weight of 1540. The reactor was purged with nitrogen and was then stirred and heated slowly to 160°–180° C. while allowing the water of reaction to distill off. The product mixture increased in viscosity until 98% of the theoretical amount of water was removed. The liquid reaction product containing

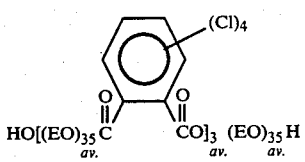

was then cooled. The product analysis showed 4.3 wt. % organic chlorine.

EXAMPLE 4

Example 3 was repeated except that 1 gram of dibutyl tin laurate catalyst was added to the components fed to the reactor. The product was the same as that obtained in Example 3 and analyzed at 4.3 wt. % organic chlorine.

EXAMPLE 5

Using the equipment described in Example 1, 194.0 grams of 4,7-methanoisobenzofuran-1,3-dione-4,5,6,7,8,8a-hexachloro-3a,4,7,7a-tetrahydro

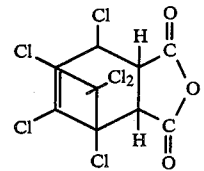

806.0 grams of polyoxyethylene molecular weight 1540, and 1.0 gram of tin oxide catalyst were added to a glass beaker. The reactor was purged with nitrogen and was then stirred and slowly heated to 160°–180° C. while allowing the water of reaction to distill off until 98% of the theoretical amount of water was removed. The reaction product containing

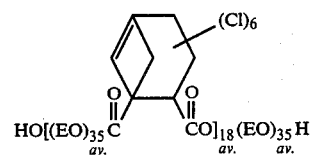

was cooled and analyzed. The organic chlorine content was found to be 11.2 wt. %.

EXAMPLE 6

Example 5 was repeated except that catalyst was omitted and 806 grams of ethylene oxide/propylene oxide polymer having a molecular weight of 1540 was substituted for ethylene oxide polymer. The product containing

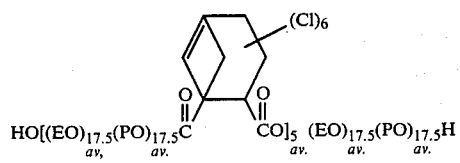

was found to have 11.2 wt. % organic chlorine.

EXAMPLE 7

Using the equipment described in Example 1, 99.0 grams of 4,7-methanoisobenzofuran-1,6-dione-4,5,6,7,8,8a-hexachloro-3a,4,7,7a-tetrahydro, 76.0 grams of 1,3-isobenzofuranedione-4,5,6,7,-tetrachloro

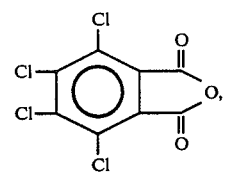

824.0 grams of polyoxyethylene having a molecular weight of 1540 and 1.0 gram of tin oxide were added to a glass flask. The system was purged with nitrogen, stirred and slowly heated to 160°–180° C. while allowing the water of reaction to distill off until 98% of the theoretical amount of water had been removed. The product containing

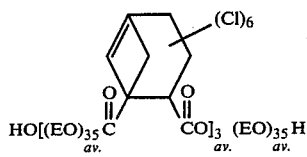

was then cooled and was analyzed at 9.5 wt. % organic chlorine.

EXAMPLE 8

Example 7 was repeated except that 824 grams of ethylene oxide/propylene oxide random polymer having a molecular weight of 1540 was subsituted for the ethylene oxide polymer. The product containing

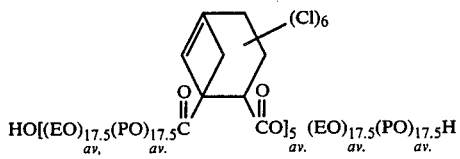

ps was found to have 9.5 wt. % organic chlorine.

EXAMPLE 9

Using the equipment and procedure described in Example 1, 110.0 grams of 4,7-methanoisobenzofuran-1,3-dione-4,5,6,7,8,8a-hexachloro-3a,4,7,7a-tetrahydro, 890.0 grams of polyoxyethylene having a molecular weight of 3000 and 1.0 gram of tin oxide were added to a glass flask. The system was purged with nitrogen and then stirred and slowly heated to 160°–180° C. while allowing the water of reaction to distill off until 98% of the theoretical amount of water had been removed. The product containing

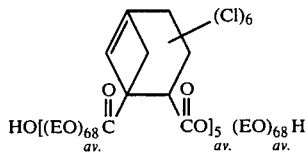

was then cooled and analyzed. The organic chlorine content was found to be 6.4 wt. %.

EXAMPLE 10

Example 9 was repeated, except that catalyst was omitted and 915.2 grams of polyoxyethylene having a molecular weight of 4000 was substituted. The product containing

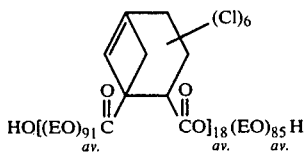

was found to contain 4.9 wt. % organic chlorine.

EXAMPLE 11

Using the procedure of Example 1, 270.0 grams of 4,7-methanoisobenzofuran-1,3-dione-4,5,6,7,8,8a-hexachloro-3a,4,7,7a-tetrahydro and 730.0 grams of polyoxyethylene having a molecular weight of 1000 were added to a glass flask, stirred, and slowly heated to 160°–180° C. while allowing water of reaction to distill off until 98% of the theoretical amount of water had been removed. The reactor contents was cooled and analyzed. The product containing

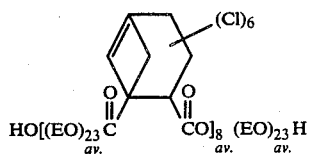

was found to have 15.8 wt. % organic chlorine.

EXAMPLE 12

Repeating the procedure of Example 1, 178.0 grams of 4,7-methanoisobenzofuran-1,3-dione-4,5,6,7,8,8a-hexachloro-3a,4,7,7a-tetrahydro, 85.2 grams of dimethyl terephthalate, and 1473.6 grams of polyoxyethylene having a molecular weight of 1540 were added to a glass flask. The resulting mixture was stirred and slowly heated to 160°–180° C. to distill off water and methanol at about 150° C. When 98% of the theoretical amount of distillate had been removed the reaction product containing

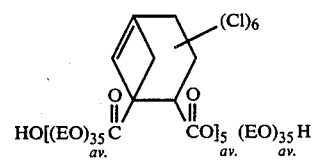

and

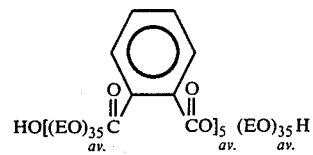

in a mole ratio of about 1:1 was cooled and analyzed. The product was found to have 6.0 wt. % organic chlorine.

EXAMPLE 13

Repeating the procedure of Example 1, 156.3 grams of 4,7-methanoisobenzofuran-1,3-dione-4,5,6,7,8,8a-hexachloro-3a,4,7,7a-tetrahydro, 119.6 grams of 1,3-isobenzofuranedione-4,5,6,7-tetrachloro, 75.1 grams of dimethyl terephthalate, 1881.3 grams of a random 1:1 ethylene oxide:propylene oxide copolymer having a molecular weight of 1540 and 1.0 gram of esterification catalyst, tin oxide, were added to a glass flask. The resulting mixture was stirred and slowly heated to 160°–180° C. while allowing water of reaction to distill off until 98% of the theoretical amount of water had been removed. The reaction product containing

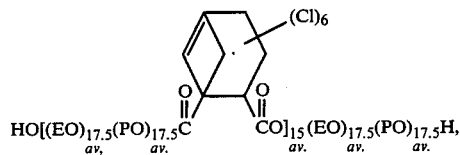

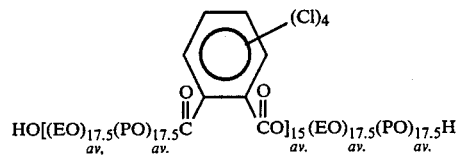

and,

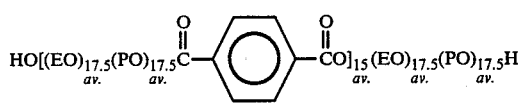

in a mole ratio of about 1:1:1 was cooled and analyzed. The product was found to have 6.6 wt. % organic chlorine.

EXAMPLE 14

Repeating the procedure of Example 1, 231.5 grams of 1,3-isobenzofuranedione-4,5,6,7,-tetrabromo, 768.5 grams of polyoxyethylene molecular weight 1540 and 1.0 gram of p-toluene sulfonic acid catalyst was added to a glass flask. The mixture was stirred and slowly heated to 160°–180° C. while allowing water of reaction to distill off until 98 wt. % of the theoretical amount of water had been removed. The reaction product containing

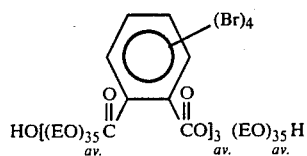

was cooled and analyzed. The product was found to have 16.1 wt. % organic bromine.

EXAMPLE 15

Repeating the procedure of Example 1, 231.5 grams of 1,3-isobenzofuranedione-4,5,6,7,-tetrabromo, 768.5 grams of a random 1:1 ethylene oxide:propylene oxide copolymer having a molecular weight of 1540 and 1.0 gram of dibutyl tin laurate catalyst were added to a glass flask. The mixture was stirred and slowly heated to 160°–180° C. while allowing water of reaction to distill off until 98% of the theoretical amount of water had been removed. The reaction product containing

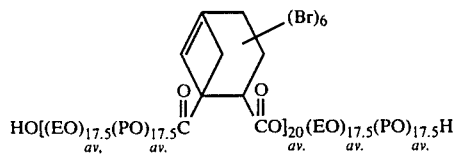

was cooled and analyzed. The product was found to have 16.1 wt. % organic bromine.

EXAMPLE 16

Repeating the procedure of Example 1, 244.7 grams of 4,7-methanoisobenzofuran-1,3-dione-5,6-dibromo-3a,4,7,7a-tetrahydro and 755.3 grams of polyoxyethylene having a molecular weight of 1000 were added to a glass flask. The mixture was stirred and slowly heated to 160°14 180° C. while allowing water of reaction to distill off until 98% of the theoretical amount of water had been removed. The reaction product containing

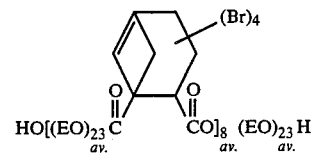

was cooled and analyzed. The product was found to have 18.3 wt. % organic bromine.

EXAMPLE 17

Repeating the procedure of Example 1, 297.3 grams of 1,3-isobenzofuranedione-4,5,6,7,-tetraiodo, 702.7 grams of polyoxyethylene having a molecular weight of 1540 and 1.0 gram of p-toluene sulfonic acid catalyst were added to glass flask. The mixture was slowly heated to 160°–180° C. while allowing water of reaction to distill off until 98% of the theoretical amount of water had been removed. The reaction product containing

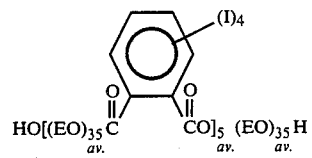

was cooled and analyzed. The product was found to have 23.6 wt. % organic iodine.

EXAMPLE 18

Repeating the procedure of Example 1, 297.3 grams of tetrachloroterephthalic acid, 702.7 grams of polyoxyethylene having a molecular weight of 1540 and 1.0 gram of p-toluene sulfonic acid catalyst were added to glass flask. The mixture was slowly heated to 160°–180° C. while allowing water of reaction to distill off until 98% of the theoretical amount of water had been removed. The reaction product containing

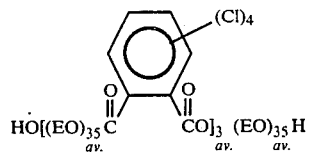

EXAMPLES 19–31

A.

STAIN REMOVAL TEST

In the following tests 12×12 inch samples of white polyester fabric were placed on a blotting paper and stained with 5 drops of an equal mixture of Nujol oil, Wesson oil, butter and mustard. A glassine paper was placed over the soiled area and a 5 lb. weight applied over the paper for 60 seconds. The samples were then placed in a washing machine filled with water to the high water level at a temperature of 140° F. One sample was employed as a control in the washing procedure. The remaining samples were treated with various soil release agents as noted in the following Table by adding 140 grams of the test material to the water. The samples were then washed in a Sears Kenmore washing machine under normal setting for 12 minutes/cycle which included washing, rinsing and spin drying. The washing cycle for each sample was repeated 25 and 50 times. After the last wash the samples were dried at 160° F. for 45 minutes and residual stains evaluated 4 hours after drying by placing the samples on a black table top and observing discoloration. The test materials were evaluated on a scale of from 1 to 5 where 5 represents substantially complete removal. The results of these tests are reported in the following Table.

B.

FLAME RETARDANCY TEST

In the following tests 12×12 inch size samples of white undyed Polyester 720 (3.1 ounces/sq. yard) was prewashed in 18 gallons of water containing 140 g. of standard detergent (AATCC 124) at 140° F. in a Sears Kenmore washing machine at normal cycle which includes washing, rinsing and spin drying. The samples were removed and dried in a Kenmore dryer at normal setting. The dried samples were the equilibrated at 65% relative humidity and 70° F. for 1 hour. The samples were then treated with various test materials as noted in the following table by applying 1 g. of test material/10 g. of polyester fabric in 200 ml of water at 180° F. and allowing the fabric to remain in the solution for 1 hour. One sample was untreated and soaked in pure water for 1 hour at 180° F.

After an hour, the samples were dried in a Kenmore dryer. The above steps of washing, drying and equilibrating were repeated on each sample for 25 and 50 wash cycles.

Each sample was then cut into 2×12 inch strips and hung on a line to dry. After drying, the flame of a bunsen burner was applied for 7 seconds to the free ends of the strips and the length of burn recorded in inches, as shown in the following Table.

C.

WATER WICKING TEST

Absorbency is an important property for fabrics used in toweling materials to be dyed or coated with various finishes.

In the present tests, the steps of washing, drying, equilibrating and impregnating 12× inch samples of Polyester 720 fabric with the various test materials, as set forth in the Fire Retardancy Test, were repeated. An untreated sample as described above was also employed as a control. The samples were then subjected to 5 wash cycles under the conditions described in test B followed by final drying in the Kenmore dryer. The samples were cut into 2×12 inch strips and the lower 1 cm of each strip was immersed in a 0.1% aqueous solution of rubine red dye. The time in seconds for the red dye to reach a 2 cm level on the strip was recorded and is reported in the following Table.

TABLE I

| Example | PRODUCT TESTED | WT. % PROD. EMPLOYED | % HALO-GEN | FLAME RETARDANCE INCHES OF SAMPLE CHARED AFTER- | | SOIL RELEASE (i) | | WATER WICKING (SECONDS) |
|---|---|---|---|---|---|---|---|---|
| | | | | 25 washes | 50 washes | 25 washes | 50 washes | 5 WASHES |
| 19 | Control | no treatment | | entire length | entire length | 2.0 | 2.5 | 5.3 |
| 20 | TDBPP (v) | 4.7 | 1.6 | 4.3 | entire length | — | — | — |
| 21 | FC-218 (ii) | 0.9 | 0.0 | entire length | entire length | 1.6 | 1.9 | 100+ |
| 22 | FC-218 + TDBPP | 15.8 | 8.4 | 4.3 | 3.7 | 3.9 | 3.0 | 100 |
| 23 | ZELCON TGF (iii) | 0.9 | 0.0 | entire length | entire length | 2.3 | 2.3 | 5.0 |
| 24 | ZELCON TGF + TDBPP | 9.8 | 6.3 | — | 5.3 | 1.5 | 1.3 | 6.7 |
| 25 | MILASE T (iv) | 11.2 | 0.0 | entire length | entire length | 4.5 | 4.0 | 3.1 |
| 26 | Prod. of Ex. 3 | 7.9 | 1.6 | — | 3.8 | 3.1 | 4.0 | 2.5 |
| 27 | Prod. of Ex. 4 | 10.9 | 2.9 | 3.4 | 4.2 | 3.1 | 2.9 | 3.0 |
| 28 | Prod. of Ex. 8 | 10.9 | 2.2 | 3.5 | 4.1 | 3.6 | 3.6 | 3.4 |
| 29 | Prod. of Ex. 1 | 11.0 | 7.9 | 3.4 | 3.9 | 3.7 | 3.4 | 3.4 |
| 30 | Prod. of Ex. 9 | 11.2 | 6.4 | 3.2 | 3.7 | 3.9 | 3.6 | 3.5 |
| 31 | Prod. of Ex. 15 | 11.3 | 16.1 | 3.6 | 4.5 | 3.9 | 3.8 | 3.2 |

(i) soil is a mixture of Nujol oil, butter, Wesson oil and mustard
(ii) a fluorocarbon fabric softener (CAS NO. 50641-94-6), supplied by 3M Co.
(iii) a yellow liquid cationic non-halogenated fabric softener, supplied by DuPont
(iv) 1,4-benzenedicarboxylic acid polymer with 1,2-ethane diol and α-hydro-w-hydroxypoly(oxy-1,2-ethanediyl)
(v) tris (2,3-dibromopropyl)phosphate

What is claimed is:

1. A textile having coated thereon an effective flame retarding amount of from about 80% to about 100% by weight of a compound having the formula

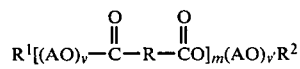

and mixtures thereof wherein AO is $C_2$ to $C_3$ alkylene oxide which, when present as a mixture of ethylene oxide and propylene oxide units can occur in random or block distribution; $R^1$ is hydroxy or $C_1$ to $C_{10}$ alkoxy; $R^2$ is hydrogen or $C_1$ to $C_{10}$ alkyl; R is a halogenated cyclic radical optionally substituted with lower alkyl and having the structure

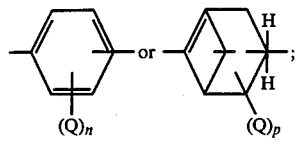

wherein Q is chlorine or bromine; n is an integer having a value of from 3 to 4; p is an integer having a value of from 2 to 6; m is an integer having a value of from 3 to 22 and v and v' are each integers having a value of from 5 to 150 and from 0% to 20% by weight of a compound having the same formula except that R is

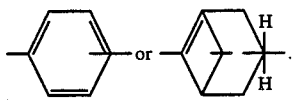

2. A process for synthesizing the compound having the formula:

$$R^1[(AO)_v-\overset{O}{\underset{\|}{C}}-R-\overset{O}{\underset{\|}{C}}]_m(AO)_{v'}R^2$$

and mixtures thereof wherein AO is $C_2$ to $C_3$ alkylene oxide which, when present as a mixture of ethylene oxide and propylene oxide units, can occur in random or block distribution; $R^1$ is hydroxy or $C_1$ to $C_{10}$ alkoxy; $R^2$ is hydrogen or $C_1$ to $C_{10}$ alkyl; R is a halogenated cyclic radical optionally substituted with lower alkyl and having the structure

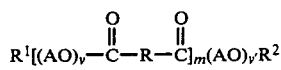

wherein Q is chlorine or bromine; n is an integer having a value of from 3 to 4; p is an integer having a value of from 2 to 6; m is an integer having a value of from 3 to 22 and v and v' are each integers having a value of from 5 to 150 which comprises reacting a cyclic halogenated dicarboxylic compound selected from the group consisting of

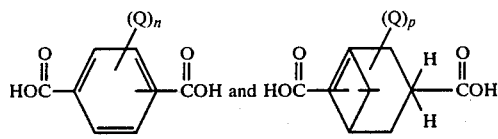

and the anhydride or lower alkyl ester derivative thereof with a polyalkyleneoxide containing terminal hydroxy groups in a mole ratio of between about 1:6 and about 1:20 at a temperature of between about 135° C. and about 220° C. under a pressure of from about 0 psia to about 50 psia to form the corresponding product of esterification while removing water of reaction and recovering said esterified product as the product of the process.

3. The process of claim 1 wherein the reaction is effected within a period of from about 2 to about 20 hours in the presence of a esterification catalyst.

4. The process of claim 3 wherein said catalyst is selected from the group of p-toluene sulfonic acid, dibutyl tin laurate and tin oxide.

5. The process of claim 2 wherein said reaction is effected at a temperature of between about 145° C. and about 200° C. at atmospheric pressure.

6. The process of claim 2 wherein said polyalkylene oxide is a mixture of polyethylene oxide and polypropylene oxide.

7. The process of claim 6 wherein the molar proportion of ethylene oxide to propylene oxide is between about 1:1.5 and about 2.5:1.

8. The process of contacting a fibrous substrate with an effective flame retarding or soil releasing amount of from about 80% to about 100% by weight of a compound having the formula $$R^1[(AO)_v-\overset{O}{\underset{\|}{C}}-R-\overset{O}{\underset{\|}{C}}O]_m(AO)_{v'}R^2$$

and mixtures thereof wherein AO is $C_2$ to $C_3$ alkylene oxide which, when present as a mixture of ethylene oxide and propylene oxide units can occur in random or block distribution; $R^1$ is hydroxy or $C_1$ to $C_{10}$ alkoxy; $R^2$ is hydrogen or $C_1$ to $C_{10}$ alkyl; R is a halogenated cyclic radical optionally substituted with lower alkyl and having the structure

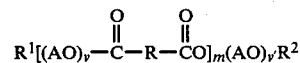

wherein Q is chlorine or bromine; n is an integer having a value of from 3 to 4; p is an integer having a value of from 2 to 6; m is an integer having a value of from 3 to 22 and v and v' are each integers having a value of from 5 to 150 and from 0% to 20% by weight of a compound having the same formula except that R is

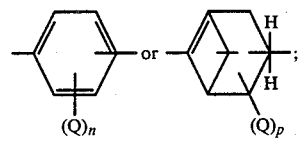

9. The process of claim 8 wherein the compound is in aqueous solution and the weight ratio of said compound to the water is about 1:99 to about 75:25.

10. The process of claim 8 wherein the substrate is cellulose.

11. The process of claim 8 wherein the substrate is a natural or synthetic fiber.

12. The process of claim 8 wherein the substrate is polyester.

13. The process of contacting a keratinous substrate with an effective soil releasing amount of from about 80% to about 100% by weight of a compound having the formula

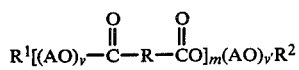

and mixtures thereof wherein AO is $C_2$ to $C_3$ alkylene oxide which, when present as a mixture of ethylene oxide and propylene oxide units can occur in random or block distribution; $R^1$ is hydroxy or $C_1$ to $C_{10}$ alkoxy; $R^2$ is hydrogen or $C_1$ to $C_{10}$ alkyl; R is a halogenated cyclic radical optionally substituted with lower alkyl and having the structure

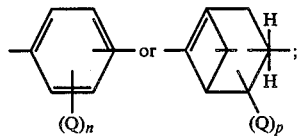

wherein Q is chlorine or bromine; n is an integer having a value of from 3 to 4; p is an integer having a value of from 2 to 6; m is an integer having a value of from 3 to 22 and v and v' are each integers having a value of from 5 to 150 and from 0% to 20% by weight of a compound having the same formula except that R is 14. The process of claim 13 where the keratinous substrate is human hair and said compound or compound mixture is incorporated in a shampoo.

15. The process of claim 13 wherein the keratinous substrate is human skin and said compound or compound mixture is incorporated in a soap.

* * * * *